United States Patent [19]

Harasymiw

[11] Patent Number: 5,126,271

[45] Date of Patent: Jun. 30, 1992

[54] METHOD FOR DETERMINING THE CONSUMPTION RATE OF ALCOHOL BY A HUMAN SUBJECT

[76] Inventor: James W Harasymiw, 1272 Balmoral Ct., Brookfield, Wis. 53005

[21] Appl. No.: 730,431

[22] Filed: Jul. 16, 1991

[51] Int. Cl.[5] .................... G01N 33/92; G01N 33/72; G01N 33/20

[52] U.S. Cl. ........................................ 436/71; 436/66; 436/79; 436/80; 436/81; 436/86; 436/88; 436/95; 436/132

[58] Field of Search .................... 436/71, 79, 132, 80, 436/81, 86, 88, 66, 95

[56] References Cited

U.S. PATENT DOCUMENTS

| | | | |
|---|---|---|---|
| 3,645,688 | 2/1972 | Smernoff | 23/230 B |
| 3,954,409 | 5/1976 | Hsia | 23/230 B |
| 4,115,062 | 9/1978 | Morre et al. | 23/230 B |
| 4,753,890 | 6/1988 | Smith-Lewis et al. | 436/74 |
| 4,820,628 | 4/1989 | Weitz | 435/4 |
| 4,820,647 | 4/1989 | Gibbons | 436/79 |
| 4,837,164 | 6/1989 | Glick | 436/88 |
| 4,952,513 | 8/1990 | Koocher | 436/36 |

OTHER PUBLICATIONS

Title: Biochemical and Hematological Correlates of Alcoholism[1] Authors; Ralph S. Ryback, Michael J. Eckardt and Charles P. Pautler Publication: Research Communication in Chemical Pathology and Pharmocology; vol 27, No. 3—Mar. 1980, pp. 533-550.

Title: Diminished Blood Selenium Levels in Alcoholics Authors: Brad M. Devorkin, MD, William S. Rosenthal, MD, Gary G. Gordon, Md, and Rita H. Jankowski, RN, MSN. Publication: Alcoholism: Clinical and Experimental Research, vol. 8, No. 6, Nov./Dec., 1984, pp. 535-538.

Title: Accelerated Turnover of Very Low Density Lipoprotein Trigycerides in Chronic Alcohol Users. Authors: Timo Sane, Esko A. Nikkila, Marja-Rutta Taskinen, Matti Valimaki and Reino Ylikahri Publication: Atherosclerosis, 53 (1984), pp. 185-193, Elsevier Scienticfic Publishers Ireland, Ltd.

Title: Plasma and Red Cell Lipids in Alcoholics with Macrocytosis Authors: M. R. Clements, W. Kessler, H. W. Schied, A. Schupmann and H. D. Waller Publication: Clincia Chimica Acta. 156 (1986), pp. 321-328, Elsevier Science Publishers B. V.

Title: Variations in HDL and VLDL Levels Chronic Alcoholics. Influence of the Degree of Liver Damage and of Withdrawal of Alcohol Authors: Sylvie Tateossian, Jacqueline G. Peynet, Alain G. Legrand, Bernadette Collet, Jean A. Rossignal, Jacques J. Delattre and Francois J. Rousselet Publication: Clinca Chimica Acta. 148 (1985), pp. 211-219, Elsevier Science Publishers, B.V.

Title: alcohol: High Density Lipoproteins, Apolipoproteins Authors: Paul Cushman, MD, Joseph Baboriak, ScD, John Kalbfliesch, PhD. Publication: Alcoholism: Clinical and Experimental Research, vol. 10, No. 1; Mar./Apr. 1986, pp. 1554-157.

Title: Decreased Serum Selenium in Alcoholics as Related to Liver Structure and Function[1-3]. Authors: Heikki Korpela, DVM, MD, Jorma Kumpulainen, PhD, Pauli V. Luoma, MD, PhD., Arno J. Arranto, MD, Phd, and Eero A. Sotaniemi, MD, PhD. Publication: The American Journal of Clinical Nutrition 42: Jul. 1985, pp. 147-151.

Title: Low Blood Selenium Levels in Alcoholics With and Without Advanced Liver Disease—Correlations with Clinical and Nutritional Status Authors: Brad Devorkin, MD, William S. Rosenthal, MD, Rita H. Jankowski, RN, MSN, Gary G. gordon, MD, and Daulat Haldea, MD Publication: Digestive Diseases and Sciences, vol. 30, No. 9, (Sep., 1985), pp. 838-844.

Title: The relationship Between Liver Function and Alcohol in Patients Admitted to an Alcoholism Unit Authors: J. R. Evans, S. Ogston, Anne Guthrie, B. Johnston and L. McKechnie Publication: Amn Clin Biochem, 1984, 21:261-267.

Title: Serum Apolipoprotein A-II, Biochemical Indicator of Alcohol Abuse Authors: Pascal Puchois, Michel Fontan, Jean-Louis Gentilini, Phillippe Gelez, Jean-Charles Fruchart Publication: Clinica Chimca Acta. 185 (1984), pp. 185-189, Elsevier Science Publications, B.V.

Title: Increased Blood Acetate: A New Laboratory Marker of Alcoholism and Heavy Drinking Authors: Ulla-Mari Korri, MD, Hannu Nuutinen, MD and Mikko Salaspuro, MB Publication: Alcoholism: Clinical and Experimental Research, vol. 9, No. 5; Sep./Oct., 1985; pp. 468-471.

(List continued on next page.)

Primary Examiner—John W. Rollins
Attorney, Agent, or Firm—Jansson & Shupe, Ltd.

[57] ABSTRACT

An improved method for determining the approximate consumption rate of alcohol by a human subject includes the steps of using are blood sample from such subject to develop a subject serum panel. Such serum panel includes at least twelve constituents, preferably more. Two of the constituents are HDL and magnesium. The subject blood serum panel is then statistically compared with a reference panel providing categories of rates of alcohol consumption such as light-to-moderate, moderate-to-heavy and very heavy. The reference panel also includes HDL and magnesium as constituents. That category of alcohol consumption which best characterizes such subject is then identified, thereby diagnosing the approximate alcohol consumption rate and, therefore, the presence or absence of probable alcohol abuse. Selenium, copper and/or zinc may also be included as constituents. Reference and subject panels may also be developed to include considerations of gender and ranges of age.

17 Claims, No Drawings

OTHER PUBLICATIONS

Title: Elevated Blood Acetate as Indicator of Fast Ethanol Elimination in Chronic Alcoholics[1] Authors: H. Nuutinen, K. Lindros, P. Hekali and M. Salaspuro Publication: Alcohol, vol. 2, 1985, pp. 623-626

Title: Carbohydrate Composition of Serum Transferrin in Alcoholic Patients Authors: Helena Stibler and Stefan Borg Publication: Alcoholism: Clinical and Experimental Research, vol. 10, No. 1; Jan./Feb. 1986, pp. 61-64.

Title: Use of Laboratory Tests to Monitor Heavy Drinking by Alcoholic Men Discharged from a Treatment Program Authors: Michael Irwin, MD, Steve Baird, MD, Tom L. Smith, PhD, and Marc Schukit, MD Publication: Am J. Psychiatry 145:5, May 1988, pp. 595-599.

Title: Differences in Platelet Enzyme Activity Between Alcoholics and NonAlcoholics Authors: Boris Tabakoff, Ph.D, Paula L. Hoffman, Ph.D, John M. Lee, Ph.D, Toshikazu Saito, MD, Ph.D, Barbera Willard, RN, and Frank DeLeon-Jones, MD Publication: The New England Journal of Medicine, Jan. 21, 1988, vol. 318, No. 3, pp. 134-139.

Title: Biological-Marker Studies in Alcoholism Author: Theodore Reich, MD Publication: The New England Journal of Medicine, Jan. 21, 1988, Vol. 318, No. 3, pp. 180-182.

Title: Biochemical Diagnosis of Alcoholism: A Test of the Discriminating Capabilities of y-Glutamyl Transpeptidase and Mean Corpuscular Volume Authors: Michael J. Eckhardt, PhD, Ralph S. Ryback, MD,. Robert R. Rawlings, MS, Barry I. Grauhard, MA Publication: JAMA, Dec. 11, 1981, vol. 246, No. 23, pp. 2707-2710.

Title: The Effectiveness of Biologic Markers to Diagose Alcoholism Authors: Ralph S. Ryback, MD, Robert R. Rawlings, MS, George L. Negron, MD, Rafael Correa-Coronas, MD, Dorothy Cirelli, MD and Sarkis Chobanian, MD Publication: "Controversies in Alcoholism and Substance Abuse", Mar. 26, 1984, pp. 191-207.

Title: Hematological Concumitants of Alcoholism: Development and Validation of a Clinical Screening Technique Authors: Michael R. Hawkins, PhD, Harry D. Silsky, MD, David J. Kruzich, PhD and Doris R. Sittig, MS Publication: Journal of Substance Abuse Treatment, vol. 1, pp. 271-276, 1984.

Title: Detection, Assessment, and Diagnosis of Alcoholism—Current Techniques Author: George R. Jacobson Title: Alcohol Consumption and High Density Lipoprotein Cholesterol Concentration Among Alcoholics Authors: Wanju S. Pai, Ronald E. Laporte, Dvid L. Hom, Lewis H. Kuller, Joyce A. D'Antonio, James P. Gutai, Marybeth Wozniczak, and Barbara Wholfohrt Published: American Journal of Epidiology, vol. 122, No. 4, pp. 620-627.

Title: Serum Zinc, Copper, and Ceruloplasmin Levels in Male Alcoholics Authors: Chao-Tsong Wu, Jau--Non Lee, Winston W. Shen and Su-Long Lee Published: Biological Psychiatry, volo. 19, No. 9, 1984, pp. 1333-1338.

Title: Average, Binge and Maximum Alcohol Intake in Healthy Young Men: Discriminant Function Analysis Authors: rich Cowan, Linda K. Massey and Thomas K. Greenfield Published: Journal of Studies on Alcohol, vol. 46, No. 6, 1985, pp. 467-472.

METHOD FOR DETERMINING THE CONSUMPTION RATE OF ALCOHOL BY A HUMAN SUBJECT

FIELD OF THE INVENTION

This invention is related generally to methods for making medical diagnoses and, more particularly, to a method for diagnosing alcoholism.

BACKGROUND OF THE INVENTION

Alcoholism is a serious human health issue and it has been predicted that it will affect about 16% of the population. Mortality rates among alcoholics are two to three times the rate for the general population and it has been suggested that it is one of the leading preventable causes of death, injury, illness and impaired functioning. In 1987, the National Institute on Alcoholism and Alcohol Abuse cited reports estimating the total societal costs for alcoholism in 1983 of about $116 billion dollars.

There are four known, major techniques for diagnosing alcoholism or excessive drinking. One of these involves the examination of blood serum variables and the remaining three involve psychological assessment.

An example of earlier work based on examination of blood serum variables is described in a paper titled "Biochemical and Hematological Correlates of Alcoholism" by Ryback et al. published in *Research Communications in Chemical Pathology and Pharmacology*. Vol. 27, No. 3, Mar. 1980. The authors considered a number of blood serum constituents in several combinations. Best accuracy (86% in the combined alcoholic group) resulted when they used the SMA 12 (12 standard constituents), SMA 6 (6 standard constituents) and Hematological (7 standard constituents) tests in combination. Table 2 of the paper shows the 25 total constituents although the authors refer in several places to the "24 tests." The authors experienced 16% "false negatives," i.e., 16% of the alcoholics were identified as being nonalcoholics. No "false positives" were experienced.

Two aspects of the Ryback et al. paper are particularly important. One is that the "prior probabilities" (a reflection of apparent historical fact) used by the authors were 0.5 for medical controls, 0.4 for treatment program alcoholics and 0.1 for alcoholics admitted to medical wards. These values were selected "arbitrarily" but were influenced by a study which indicated that about 50% of a group of patients admitted to a Veterans Hospital had alcohol related problems.

The authors further indicate that adjustment of the prior probabilities by + or −0.1 resulted in no significant change in the accuracy of the discrimination between alcoholics and nonalcoholics. They also stated that "[t]he prior probabilities could be changed from 0.4 to 0.8 in the medical controls and from 0.6 to 0.2 in the alcoholics with no significant change in the accuracy of discrimination."

The other particularly important aspect of the Ryback et al. paper is a quotation appearing on page 545. There, the authors state that "[s]ignificant relationships involving drinking variables were observed for all tests *except* cholesterol . . . " (emphasis added).

Another relevant paper dealing with examination of blood serum variables is titled "Hematological Concomitants of Alcoholism: Development and Validation of a Clinical Screening Technique" by Hawkins et al. published in *Journal of Substance Abuse Treatment*, Vol. 1, 1984. While the age and sex of the subjects were noted, no observation was made as to whether such factors are of use in identifying abuse. Hawkins et al. used two different multivariate discriminant analyses which yielded classification accuracies significantly different from one another. The quadratic analysis correctly classified about 94% of alcoholics while the "stepwise" analysis correctly classified about 79% of alcoholics.

The authors' caveat states". . . this technique is unlikely to provide sufficiently precise classification for anything other than medical screening purposes, which should then be bolstered with independent substantiation before arriving at a diagnosis."

Some of the earlier work involving analysis of blood serum variables considers the blood chemistry constituents selenium and magnesium. Such work is described in a paper titled "Diminished Blood Selenium Levels in Alcoholics" by Dworkin et al. published in *Alcoholism: Clinical and Experimental Research*, Vol. 8, No. 6, Nov./Dec. 1984. The authors have noted that alcoholics have a reduced level of selenium. As stated in the Abstract, this fact is of concern to the authors "[s]ince selenium deficiency can produce a spectrum of organ injury . . . the relationship of selenium deficiency to alcohol-induced organ injury deserves further study."

Clearly, the subjects had *already* been identified as alcohol abusers—the focus of the research was prospective organ damage. And the authors observe that low selenium levels can also result from diet, cancer, severe burns and kwashiorkor. In other words, a low selenium blood serum level per se was not appreciated as having value in the diagnosis of alcohol abuse. A similar paper is "Decreased Serum Selenium in Alcoholics as Related to Liver Structure and Function" by Korpela et al. published in *The American Journal of Clinical Nutrition*, Jul. 1985.

Other work involving blood serum variables is described in a paper titled "Serum Zinc, Copper, and Ceruloplasmin Levels in Male Alcoholics" by Wu et al. published in *Biological Psychiatry*, Vol. 19, NO. 9, 1984. The authors used blood samples from known alcoholics having an average daily consumption level of about 294 mL of absolute alcohol. They noted the reciprocal relationship between serum zinc and copper levels and found that the serum zinc level in alcoholic patients was lower than that of a control group. While the serum copper level was higher, the authors indicate it was not statistically significant. The authors also observe that earlier workers have found a psychiatric condition, i.e., depression, to be associated with lower serum zinc levels and low zinc, copper and ceruloplasmin levels. In an added note, the authors also state, with respect to serum levels of calcium and magnesium, that "[t]heir differences were *not* statistically significant between alcoholics and controls."

Yet another paper dealing with blood serum variables is titled "Alcohol Consumption and High Density Lipoprotein Cholesterol Concentration Among Alcoholics" by Dai et al. published in *American Journal of Epidemiology*, Vol. 122, No. 4, 1985. In the Abstract, the authors note that HDL cholesterol increased with increasing alcohol consumption up to about 450 mL of ethanol consumption per day. Above such consumption level, HDL cholesterol level decreased or appeared to decrease. The authors primarily examined the relationship between alcohol consumption and the level of HDL subclasses HDL2 and HDL3.

Currently, most persons suspected of having a drinking problem are screened using psychological tests, some of which are mentioned below. A frequent difficulty with such tests is that their results depend heavily upon the subject's "good will," i.e., information as voluntarily disclosed by the subject. Since denial is a frequent trait of alcoholics, such information can be "skewed" and accuracy of diagnosis suffers.

One psychological approach, empirical in nature, is known as the MacAndrew scale of the Minnesota MultiPhasic Personality Inventory (MMPI). The MacAndrew scale is generally accepted as a reliable method of alcohol assessment. It has been demonstrated to correctly classify about 84% of alcoholics when a cutoff score of 24 raw points is used. There are about 10 false negatives and 14 false positives using such cutoff point.

In general, the MacAndrew test is composed of those items from the MMPI to which alcoholics respond differently than does the general population. The subject is required to respond to "true" or "false" questions which include latent "check" questions to detect whether the subject has answered consistently. The accuracy of the MacAndrew scale has been questioned since it also seems to respond to other forms of drug addiction as well as to general deviancy.

It should be appreciated that when tests are used for certain purposes, e.g., screening job applicants, "false positives" present a certain risk for the tester. The applicant may be denied a job, perhaps one of substantial responsibility, if s/he is falsely said to be alcoholic. The authors of the aforementioned Ryback et al. paper refer to this happenstance as "clinically embarrassing."

On the other hand, there are situations where a false positive causes little or no adversity to anyone but the risk of a false negative is relatively great. For example, alcoholism in persons under consideration for alcoholism treatment should be identified with a relatively high level of certainty. Another example involves selection of persons for highly sensitive tasks requiring, e.g., certain unusual physical skills or a high level of secrecy. The public interest in selection accuracy may be sufficiently high so as to outweigh considerations of adversity arising from a false positive. In those instances, the sole question is whether the subject is drinking alcoholically rather than how much (within quantity ranges) the subject is drinking. Identification of such individuals is by using only two prior probability values, namely, 0.5 and 0.5 rather than the more typical 0.9 and 0.1 values. As described herein in connection with the invention, the use of three prior probability values aids in identifying how much the subject is drinking.

Another psychological approach involves the use of "consumption pattern" questionnaires. The Khavari Alcohol Test is an example of such an approach. In studies of validity and reliability, the Khavari test has consistently and relatively accurately differentiated between alcoholic and control groups. The Khavari test considers the drinking patterns of individuals (as provided by such individuals) and compares such patterns with established statistical drinking norms. These comparisons are then used for making diagnostic decisions.

Yet another psychological approach involves a variety of questionnaires which attempt to count incidents of problems or behaviors thought to be symptomatic of alcoholism. The Michigan Alcoholism Screening Test (MAST), and the National Council on Alcoholism Criteria for the Diagnosis of Alcoholism (CRIT) are examples. In a modified form known as MODCRIT, the latter is used clinically.

U.S. Pat. Nos. 3,954,409 (Hsia), 3,645,688 (Smernoff), 4,115,062 (Morre et al.), 4,820,628 (Weitz), 4,753,890 (Smith-Lewis et al.), 4,820,647 (Gibbons) and 4,837,164 (Glick) describe methods for analyzing blood serum constituents. Such patents do not suggest how such methods might be used for determining the consumption rate of alcohol or for diagnosing alcoholism.

The Smernoff and Hsia patents involve cholesterol in blood and describe methods for recognizing the type and presence of hyperlipoproteinemia (Smernoff) or for assessing the risk of coronary heart disease (Hsia). The Smith-Lewis et al. patent describes a method for determining magnesium ions in, among other things, blood serum and plasma. While the patent says the determination of such ion can be used for diagnosing and treating "various ailments," alcohol abuse is neither mentioned nor suggested.

An aspect of the earlier work described above may be summarized by observing that it fails to appreciate how the actual "level" or rate (within somewhat broad ranges) at which an individual is consuming ethanol alcohol can be relatively quickly determined by analyzing the serum variables in a blood sample taken from such individual. A method for making such a determination would be an important advance in diagnosing alcoholism. This is especially true if the level of accuracy is sufficient to permit the method to be the sole, or at least predominant, clinical tool in diagnosing alcoholism.

OBJECTS OF THE INVENTION

It is an object of this invention to provide an improved method for determining the rate of consumption of alcohol which overcomes some of the problems and shortcomings of the prior art.

Another object of this invention is to provide an improved method for determining the rate of consumption of alcohol which is objective in nature in that it does not rely upon the "good will" of the subject individual.

Yet another object of this invention is to provide an improved method for determining alcohol consumption rate which can serve as the sole, or at least the predominant, tool in diagnosing alcoholism.

Another object of this invention is to provide an improved method for determining alcohol consumption rate which is relatively quickly and easily utilized in making alcoholism diagnoses.

These and other important objects will be apparent from the following description.

SUMMARY OF THE INVENTION

The improved method for determining the approximate consumption rate of alcohol by a human subject includes the steps of using a blood sample from such subject to develop a subject serum panel including at least twelve constituents, two of which are HDL and magnesium. The subject panel is compared with a reference panel providing categories of alcohol consumption and including HDL and magnesium as constituents. That category of alcohol consumption is then identified which best characterizes the subject so that the presence or absence of probable alcohol abuse is diagnosed.

In a highly preferred method, the reference panel is developed using a relatively large pool of human subjects and using prior probability values selected in view of the likelihood that a subject would be classified in a particular category of alcohol consumption. In one aspect of the method, there are three categories of alcohol consumption and such categories are correlated to an increasing consumption rate of alcohol per unit time. Preferred prior probability values are between 0.80 and 0.90 for that category reflecting the lowest consumption rate, between 0.08 and 0.12 for that category reflecting the intermediate consumption rate and between 0.01 and 0.06 for that category reflecting the highest consumption rate. Highly preferred values within the aforementioned ranges are about 0.84, about 0.1 and about 0.04, respectively.

The accuracy of the new method is further enhanced where the reference panel and the subject panel include selenium, copper and/or zinc as an element (or elements) of analysis. And accuracy increases with the inclusion of each such additional element.

The persons used to develop the reference panel are preliminarily grouped into one of two classification variables related to alcohol consumption, i.e., abusive and non-abusive categories. Such grouping is by using a psychological test, preferably selected from a group of such tests including the Khavari Alcohol Test, the MacAndrew scale and MODCRIT. Of these, the Khavari Alcohol Test is preferred for reasons explained in the detailed description.

Accuracy is also improved where the reference panel is developed using a relatively large number of subjects, namely, at least several hundred subjects and preferably about 1200 subjects. The reference serum panel may include the widely-recognized SMA 6, SMA 12 and hematological tests although other similar, common tests may also be used to develop such reference serum panel.

Still other refinements of the new method involve development of reference and subject serum panels using, in addition to "common" serum elements, ranges of age and/or gender factors. Further details of the new method are set forth in the following detailed description.

DETAILED DESCRIPTIONS OF THE PREFERRED EMBODIMENTS

A purpose of the new method is to provide a "mechanism" for determining an individual's actual alcohol consumption level based upon certain blood constituents (or "variables" as they are sometimes called) and upon the quantity of such constituents compared to a reference. Such constituents are included in what is known as a "panel," i.e., a listing of constituents such as glucose, albumin, red blood count and the like which are present (as detected by lab analysis) in blood serum. For a given blood sample, each constituent is accompanied by an indication of the quantity of such constituent (usually per unit of volume) found in the sample. Of course, each constituent (or "variable") can—and does—vary from person to person and from time to time for a particular person. So-called "normal" ranges recognize the possibility of such variations.

The new method includes the development of a standard or reference panel with which actual panels derived from actual blood samples are compared in a particular way. The reference panel would include not only the "normal" range of values for each serum constituent but would also include at least two other ranges for each constituent. These additional ranges relate to "heavy" and "very heavy" consumption rates, respectively, of ethanol, the type of alcohol in alcoholic beverages.

The new method involves the inclusion of two or more additional blood serum constituents in the reference panel and in the panel developed from an actual blood sample of a subject. Such constituents were selected because each of them responds (in the amount of the constituent present in the serum) to the general level of alcohol consumption. Such response is not necessarily linear and in at least most instances is distinctly non-linear.

Equally important is the fact that such variables are less affected by other events occurring in the body. To put it another way, they tend to be relatively "alcohol-specific" in the way the blood serum level of each of them changes.

The preferred variables are high density lipoprotein (HDL) and magnesium. The blood serum level of HDL increases with heavy drinking while that of magnesium or selenium decreases. Selenium, copper and/or zinc may be additional variables. In general, the levels of selenium and zinc decline with heavy drinking while the level of copper increases.

The standard or reference blood serum panel is developed by identifying a relatively large number of persons (who are free of liver disease), at least several hundred up to perhaps twelve hundred or so. The increased "sample size" helps improve accuracy. One preferred reference panel includes (with minor differences) SMA6, SMA 12 and hematological tests and it also includes HDL and magnesium as constituents.

However, it should be appreciated that but for the inclusion of additional elements as described in connection with the invention, the precise makeup of the reference panel is not especially critical. For example, many laboratories offer blood serum analysis services and provide their own panel "construction." So long as the panel includes at least, say, twelve elements (and preferably more than twenty) and so long as most of those elements are those commonly considered for diagnostic purposes, the panel is acceptable.

Such persons (which will be taken from populations having, by percent distribution, known drinking habits) are preliminarily grouped into one of two classification variables, i.e., abusive drinker and non-abusive drinker categories, using one of several available psychological tests. Notwithstanding accepted test methodology, a formerly-abusive drinker is grouped into the non-abusive drinker category only if s/he had been abstinent for at least 8 weeks rather than the customary 2-3 weeks or so.

Preferred psychological tests include the Khavari Alcohol Test, the MacAndrew scale and MODCRIT. Of this group, the Khavari test is most preferred. A feature of the Khavari test is that it elicits information from the subject which enables annual consumption rates of absolute alcohol (ethanol) to be closely estimated. Annual consumption of ethanol is organized according to three groupings which become the second classification variable. The Khavari test also includes "check" questions which aid greatly in assessing the veracity of the respondent.

In accordance with the Khavari test, consumption of 0-590 oz. ethanol annually comprises Group 3, light-to-moderate. Consumption of 591-1180 oz. annually comprises Group 2, moderate-to-heavy, while consumption of more than 1180 oz. annually comprises Group 1, very heavy. These consumption rates represent one, two and more than two standard deviations above the mean, respectively.

After all drinkers in the relatively large group of subjects are identified and organized as described above, blood samples are taken from each person in each group and are analyzed. Correlation of each sample (and its analysis) to the relevant group i.e., Group 3, 2 or 1 is maintained so that the reference "norms" are accurately related to the group responsible for the data.

Prior probability values are then assigned for categorization in Group 3, 2 or 1 and the preferred values are between 0.8 and 0.9, between 0.08 and 0.12 and between 0.01 and 0.06 for Groups 3, 2 and 1, respectively. Within those ranges, prior probability values of about 0.86, 0.1 and 0.04, respectively, are highly preferred. Fundamentally, such values respond to the question, "What are the chances that a person belongs in a particular group?" and are consistent with the level of alcohol consumption in the general population. Such values are a significant factor in enabling the new method to be used as a broadly applicable diagnostic tool by institutions and care providers which deal with the general population.

The next step in preparing the reference blood serum panel is the performance of a discriminant analysis upon the individual panels of the relatively large number of persons selected to form the "reference" base. The preferred statistical procedure is the DISCRIM computer program, from the Statistical Package for Social Science (SPSS) PC+ statistical package available from SPSS, Inc. in Chicago. However, there are other statistical analysis programs which serve well for such analysis.

These steps result in a "standard" or reference blood serum panel which lists constituents and provides reference ranges for each constituent and for each of the three consumption levels, i.e., light-to-moderate, moderate-to-heavy and very heavy. The new method may be further refined by the inclusion of gender and age categories as additional variables to further enhance accuracy of the method. Preferred age categories are 18-35, 36-64 and over 64 years of age.

After the reference panel is developed, the tester is ready to use the method on actual subjects. To do so, a blood sample is drawn from a subject and used to develop a subject blood serum panel. Such serum panel is preferably constituted like the individual panels used to develop the reference panel. The subject panel is then compared by statistical analysis with the reference panel and the deviations noted.

The results are impressive. In experiments using the new blood serum panel (which includes HDL and magnesium) and prior probabilities, 100% of the moderate drinkers were correctly identified as belonging in that group 85.7% of the heavy drinkers were correctly identified as belonging in that group and 81.8% of the very heavy or alcoholic drinkers were correctly identified as belonging in that group. The method resulted in no false positives when used with the three preferred prior probability ranges indicated.

As noted above, this can be an important fact since blood serum analyses are often performed as part of, for example, a job application. The absence of false positives helps assure a licensee-user of the method that test results will not falsely indicate a person is drinking heavily when, in fact, they are not. Risk of loss of a job opportunity for reasons relating to drinking habits are thereby avoided.

Another impressive aspect of the new method is that it significantly improves upon the Ryback et al. method. For example, using the Ryback et al. blood serum panel and prior possibilities (and noting that Ryback uses only two groupings), the inventive method correctly identified 91.8% of the alcohol abusive group as belonging in that group. In contrast, the Ryback et al. method resulted in correct identification of about 86% as belonging in that group.

Using the Ryback et al. blood serum panel and the highly preferred prior possibilities mentioned above, the new method correctly identified 77% of the alcohol abusive group as belonging in that group. However, using the blood serum panel of the invention with the Ryback et al. prior possibilities, the new method nevertheless correctly identified 97.2% of the alcohol abusive group as belonging in that group. This demonstrates that even with prior probabilities which are incorrect for the general population, the new method yields excellent results.

While the principles of this invention have been described in connection with specific embodiments, it should be understood clearly that these descriptions are made only by way of example and are not intended to limit the scope of the invention.

I claim:

1. An improved method for determining the approximate consumption rate of alcohol by a human subject including the steps of:
    using a blood sample from such subject to develop a subject serum panel including at least twelve constituents, two of which are HDL and magnesium;
    comparing such subject panel with a reference panel developed using psychological factors and providing categories of alcohol consumption and including HDL and magnesium as constituents; and,
    identifying that category of alcohol consumption which best characterizes such subject,
    whereby the presence or absence of probable alcohol abuse is diagnosed.

2. The method of claim 1 wherein such reference panel is developed using a relatively large pool of human subjects and prior probability values selected in view of the likelihood that a subject would be classified in a particular category of alcohol consumption.

3. The method of claim 2 wherein there are three categories of alcohol consumption, wherein such categories are correlated to an increasing consumption rate of alcohol per unit time and wherein such prior probability values are:
    between 0.80 and 0.90 for that category reflecting the lowest consumption rate;
    between 0.08 and 0.12 for that category reflecting the intermediate consumption rate; and,
    between 0.01 and 0.06 for that category reflecting the highest consumption rate.

4. The method of claim 3 wherein such prior probability values are about 0.84 for that category reflecting the lowest consumption rate, about 0.1 for that category reflecting the intermediate consumption rate and about 0.04 for that category reflecting the highest consumption rate.

5. The method of claim 1 wherein the reference serum panel further includes selenium.

6. The method of claim 1 wherein the reference serum panel further includes copper.

7. The method of claim 1 wherein the reference serum panel further includes zinc.

8. The method of claim 1 wherein the subjects used to develop the reference panel are preliminarily grouped into one of two classification variables related to alcohol consumption.

9. The method of claim 8 wherein such classification variables include abusive and non-abusive categories.

10. The method of claim 9 wherein such factors involve a psychological test selected from a group of such tests including the Khavari Alcohol Test, the MacAndrew scale and MODCRIT.

11. The method of claim 10 wherein such psychological test is the Khavari Alcohol Test.

12. The method of claim 1 wherein such reference panel is developed using a relatively large number of subjects.

13. The method of claim 12 wherein at least several hundred subjects are used.

14. The method of claim 13 wherein about 1200 subjects are used.

15. The method of claim 1 wherein the subject serum panel includes at least one element selected from a group of elements including selenium, copper and zinc.

16. The method of claim 1 wherein such reference panel is developed using ranges of age.

17. The method of claim 1 wherein such reference panel is developed based on gender.

* * * * *

UNITED STATES PATENT AND TRADEMARK OFFICE
CERTIFICATE OF CORRECTION

PATENT NO. : 5,126,271
DATED : June 30, 1992
INVENTOR(S) : James W. Harasymiw It is certified that error appears in the above-identified patent and that said Letters Patent is hereby corrected as shown below:

ON THE TITLE PAGE

In the Abstract, line 3, delete "are" and insert --a--.

Signed and Sealed this

Tenth Day of August, 1993

Attest:

MICHAEL K. KIRK

*Attesting Officer*  *Acting Commissioner of Patents and Trademarks*